US009271487B2

(12) United States Patent
Topolkaraev et al.

(10) Patent No.: US 9,271,487 B2
(45) Date of Patent: *Mar. 1, 2016

(54) PROTEIN STABILIZED ANTIMICROBIAL COMPOSITION FORMED BY MELT PROCESSING (71) Applicant: Kimberly-Clark Worldwide, Inc., Neenah, WI (US)

(72) Inventors: Vasily A. Topolkaraev, Appleton, WI (US); Neil T. Scholl, Neenah, WI (US); Jaehong Lee, Gyeonggi-do (KR); Dianna L. Ambrose, Neenah, WI (US); YoungSook Kim, Gyeonggi-do (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 2 days.

This patent is subject to a terminal disclaimer.

(21) Appl. No.: 13/899,615

(22) Filed: May 22, 2013

(65) Prior Publication Data

US 2013/0251776 A1    Sep. 26, 2013

Related U.S. Application Data (62) Division of application No. 12/961,634, filed on Dec. 7, 2010, now Pat. No. 8,524,264.

(51) Int. Cl.
*A01N 25/02* (2006.01)
*A01N 25/10* (2006.01)
(Continued)

(52) U.S. Cl.
CPC ............. *A01N 25/02* (2013.01); *A01N 31/08* (2013.01); *A01N 43/90* (2013.01); *A01N 65/00* (2013.01);
(Continued)

(58) Field of Classification Search
None
See application file for complete search history.

(56) References Cited

U.S. PATENT DOCUMENTS 3,351,531 A * 11/1967 Noznick et al. ............... 424/491
3,354,506 A    11/1967 Raley
(Continued)

FOREIGN PATENT DOCUMENTS

EP    0388718 A2    9/1990
EP    0388718 A3    9/1990
(Continued)

OTHER PUBLICATIONS

Mastromatteo et al. (Innovative Food Science and Emerging Technologies, 2009;10:222-227).*
(Continued)

*Primary Examiner* — Ernst V Arnold
(74) *Attorney, Agent, or Firm* — Dority & Manning, P.A.

(57) ABSTRACT

A method for forming an antimicrobial composition that includes mixing an antimicrobially active botanical oil (e.g., thymol, carvacrol, etc.) and protein within a melt blending device (e.g., extruder) is provided. Despite the problems normally associated with melt processing proteins, the present inventors have discovered that the processing conditions and components may be selectively controlled to allow for the formation of a stable, melt-processed composition that is able to exhibit good mechanical properties. For example, the extrusion temperature(s) and shear rate employed during melt blending are relatively low to help limit polypeptide dissociation, thereby minimizing the impact of aggregation and embrittlement. While the use of such low temperature/shear conditions often tend to reduce mixing efficiency, the present inventors have discovered that a carrier fluid may be employed to enhance the ability of the botanical oil to flow into the internal structure of the protein where it can be retained in a stable manner. The composition is also typically anhydrous and generally free of solvents. In this manner, the protein will not generally disperse before use and prematurely release the botanical oil.

20 Claims, 3 Drawing Sheets (51) Int. Cl.
*A01N 25/12* (2006.01)
*A01N 25/28* (2006.01)
*A01N 25/34* (2006.01)
*A01N 43/90* (2006.01)
*A01N 65/00* (2009.01)
*B29B 7/42* (2006.01)
*B29C 47/00* (2006.01)
*B29C 47/02* (2006.01)
*B29C 47/60* (2006.01)
*B29C 47/92* (2006.01)
*A01N 31/08* (2006.01)

(52) U.S. Cl.
CPC .............. *B29B 7/42* (2013.01); *B29C 47/0004* (2013.01); *B29C 47/0009* (2013.01); *B29C 47/0021* (2013.01); *B29C 47/0026* (2013.01); *B29C 47/025* (2013.01); *B29C 47/6056* (2013.01); *B29C 47/92* (2013.01); *B29C 2947/926* (2013.01); *B29C 2947/92514* (2013.01); *B29C 2947/92704* (2013.01); *B29C 2947/92828* (2013.01); *B29C 2947/92876* (2013.01)

(56) References Cited

U.S. PATENT DOCUMENTS

| | | |
|---|---|---|
| 3,494,821 A | 2/1970 | Evans |
| 3,650,649 A | 3/1972 | Schippers |
| 3,801,429 A | 4/1974 | Schrenk et al. |
| 3,973,695 A | 8/1976 | Ames |
| 4,100,324 A | 7/1978 | Anderson et al. |
| 4,144,370 A | 3/1979 | Boulton |
| 4,652,441 A | 3/1987 | Okada et al. |
| 4,690,825 A | 9/1987 | Won |
| 4,695,450 A | 9/1987 | Bauer et al. |
| 4,820,435 A | 4/1989 | Zafiroglu |
| 5,023,080 A | 6/1991 | Gupta |
| 5,057,361 A | 10/1991 | Sayovitz et al. |
| 5,179,164 A | 1/1993 | Lausberg et al. |
| 5,240,764 A | 8/1993 | Haid et al. |
| 5,284,703 A | 2/1994 | Everhart et al. |
| 5,320,669 A | 6/1994 | Lim et al. |
| 5,330,768 A | 7/1994 | Park et al. |
| 5,350,624 A | 9/1994 | Georger et al. |
| 5,354,726 A | 10/1994 | Narayanan et al. |
| 5,395,055 A | 3/1995 | Shutov et al. |
| 5,397,834 A | 3/1995 | Jane et al. |
| 5,421,898 A | 6/1995 | Cavanagh |
| 5,523,293 A | 6/1996 | Jane et al. |
| 5,589,195 A | 12/1996 | Potter |
| 5,665,428 A | 9/1997 | Cha et al. |
| 5,687,875 A | 11/1997 | Watts et al. |
| 5,702,717 A | 12/1997 | Cha et al. |
| 5,723,588 A | 3/1998 | Donofrio et al. |
| 5,735,588 A | 4/1998 | Dittman et al. |
| 5,785,179 A | 7/1998 | Buczwinski et al. |
| 5,871,872 A | 2/1999 | Matijevic et al. |
| 5,882,702 A | 3/1999 | Abdel-Malik et al. |
| 5,919,471 A | 7/1999 | Saferstein et al. |
| 5,928,661 A | 7/1999 | Fujita et al. |
| 5,964,351 A | 10/1999 | Zander |
| 6,030,331 A | 2/2000 | Zander |
| 6,090,925 A | 7/2000 | Woiszwillo et al. |
| 6,121,165 A | 9/2000 | Mackey et al. |
| 6,133,166 A | 10/2000 | Nissing et al. |
| 6,158,614 A | 12/2000 | Haines et al. |
| 6,238,682 B1 | 5/2001 | Klofta et al. |
| 6,269,969 B1 | 8/2001 | Huang et al. |
| 6,269,970 B1 | 8/2001 | Huang et al. |
| 6,270,878 B1 | 8/2001 | Wegele et al. |
| 6,273,359 B1 | 8/2001 | Newman et al. |
| 6,315,864 B2 | 11/2001 | Anderson et al. |
| 6,523,690 B1 | 2/2003 | Buck et al. |
| 6,568,625 B2 | 5/2003 | Faulks et al. |
| 6,589,549 B2 | 7/2003 | Shih et al. |
| 6,719,995 B2 | 4/2004 | Rajaiah et al. |
| 6,766,919 B2 | 7/2004 | Huang et al. |
| 6,770,433 B2 | 8/2004 | Hioki |
| 6,806,213 B2 | 10/2004 | Brooks |
| 6,806,353 B2 | 10/2004 | Zhang et al. |
| 6,824,734 B2 | 11/2004 | Boggs et al. |
| 6,989,149 B2 | 1/2006 | Glenn, Jr. et al. |
| 7,127,771 B2 | 10/2006 | McDevitt et al. |
| 7,250,152 B2 | 7/2007 | Gentile et al. |
| 7,338,927 B2 | 3/2008 | Shapiro |
| 7,462,348 B2 | 12/2008 | Gruenbacher et al. |
| 7,560,422 B2 | 7/2009 | Shapiro |
| 7,605,096 B2 | 10/2009 | Tomarchio et al. |
| 7,612,029 B2 | 11/2009 | Foland et al. |
| 7,614,812 B2 | 11/2009 | Reddy et al. |
| 7,662,409 B2 | 2/2010 | Masters |
| 7,803,413 B2 | 9/2010 | van Lengerich et al. |
| 7,803,414 B2 | 9/2010 | Van Lengerich et al. |
| 7,998,888 B2 | 8/2011 | Shi et al. |
| 2002/0160035 A1 | 10/2002 | Fotinos |
| 2003/0031722 A1 | 2/2003 | Cao et al. |
| 2003/0082219 A1 | 5/2003 | Warren et al. |
| 2003/0105207 A1 | 6/2003 | Kleyer et al. |
| 2003/0135172 A1 | 7/2003 | Whitmore et al. |
| 2003/0206942 A1 | 11/2003 | Kulkarni et al. |
| 2004/0018241 A1 | 1/2004 | Houze et al. |
| 2004/0026289 A1 | 2/2004 | Halkyard |
| 2004/0037870 A9 | 2/2004 | Fotinos |
| 2004/0043134 A1 | 3/2004 | Corriveau et al. |
| 2004/0234609 A1 | 11/2004 | Collier et al. |
| 2004/0255408 A1 | 12/2004 | Norton et al. |
| 2005/0048121 A1 | 3/2005 | East et al. |
| 2005/0158369 A1 | 7/2005 | Dorschner et al. |
| 2005/0214349 A1 | 9/2005 | Nie et al. |
| 2005/0238591 A1 | 10/2005 | Sagel et al. |
| 2005/0245162 A1 | 11/2005 | McCormack et al. |
| 2006/0062832 A1 | 3/2006 | Lopes |
| 2006/0128248 A1 | 6/2006 | Ellis |
| 2007/0224261 A1 | 9/2007 | Draper |
| 2007/0254035 A1 | 11/2007 | Hao et al. |
| 2007/0256247 A1 | 11/2007 | Privitera et al. |
| 2007/0269567 A1 | 11/2007 | McMindes et al. |
| 2008/0160084 A1 | 7/2008 | Huynh et al. |
| 2008/0200359 A1 | 8/2008 | Smets et al. |
| 2008/0207481 A1 | 8/2008 | Meine et al. |
| 2008/0221003 A1 | 9/2008 | Meine et al. |
| 2009/0087468 A1 | 4/2009 | Stephenson et al. |
| 2009/0136555 A1 | 5/2009 | Crowley et al. |
| 2009/0175806 A1 | 7/2009 | Modak et al. |
| 2009/0186096 A1 | 7/2009 | Kritzman et al. |
| 2009/0196909 A1 | 8/2009 | Cooper et al. |
| 2009/0226530 A1 | 9/2009 | Lassner et al. |
| 2009/0232905 A1 | 9/2009 | Weiss et al. |
| 2009/0286437 A1 | 11/2009 | Cunningham et al. |
| 2009/0297664 A1 | 12/2009 | Forte et al. |
| 2010/0034907 A1 | 2/2010 | Daigle et al. |
| 2010/0065445 A1 | 3/2010 | Stevenson |
| 2010/0101605 A1 | 4/2010 | Saint Victor |
| 2010/0136201 A1 | 6/2010 | Bigeard et al. |
| 2010/0144584 A1 | 6/2010 | Saint Victor |
| 2010/0159170 A1 | 6/2010 | Wang et al. |
| 2010/0234517 A1 | 9/2010 | Plantenberg et al. |
| 2010/0240724 A1 | 9/2010 | Chang et al. |
| 2010/0240799 A1 | 9/2010 | Hofmann et al. |
| 2010/0247371 A1 | 9/2010 | Farrugia et al. |
| 2010/0272831 A1 | 10/2010 | Lagaron-Cabello et al. |
| 2011/0086084 A1 | 4/2011 | Koenig et al. |
| 2011/0086085 A1 | 4/2011 | Wenzel et al. |
| 2011/0150955 A1 | 6/2011 | Klingman |
| 2012/0141567 A1 | 6/2012 | Wang et al. |
| 2012/0141569 A1 | 6/2012 | Lee et al. |

(56) References Cited

U.S. PATENT DOCUMENTS

| | | | |
|---|---|---|---|
| 2012/0141571 A1 | 6/2012 | Lee et al. | |
| 2012/0141609 A1 | 6/2012 | Topolkaraev et al. | |

FOREIGN PATENT DOCUMENTS

| | | | |
|---|---|---|---|
| EP | 0504387 | B1 | 7/1995 |
| EP | 0863942 | B1 | 9/1998 |
| EP | 1004703 | A1 | 5/2000 |
| EP | 1023863 | A1 | 8/2000 |
| EP | 1059032 | A1 | 12/2000 |
| EP | 1059378 | A1 | 12/2000 |
| EP | 1275370 | A1 | 1/2003 |
| EP | 1275371 | A1 | 1/2003 |
| EP | 1408926 | B1 | 4/2004 |
| EP | 1618240 | B1 | 1/2006 |
| EP | 1624013 | A1 | 2/2006 |
| EP | 1757261 | A2 | 2/2007 |
| EP | 1757261 | A3 | 2/2007 |
| EP | 1867317 | A2 | 12/2007 |
| EP | 1867317 | A3 | 12/2007 |
| FR | 2900940 | A1 | 11/2007 |
| GB | 2444112 | A | 5/2008 |
| WO | WO 9003784 | A1 | 4/1990 |
| WO | WO 9205708 | A1 | 4/1992 |
| WO | WO 0151557 | A1 | 7/2001 |
| WO | WO 02074430 | A1 | 9/2002 |
| WO | WO 2006000032 | A1 | 1/2006 |
| WO | WO 2007135273 | A2 | 11/2007 |
| WO | WO 2007135273 | A3 | 11/2007 |
| WO | WO 2008030969 | A2 | 3/2008 |
| WO | WO 2008030969 | A3 | 3/2008 |
| WO | WO 2008063088 | A1 | 5/2008 |
| WO | WO 2008063088 | A8 | 5/2008 |
| WO | WO 2008149232 | A2 | 12/2008 |
| WO | WO 2008149232 | A3 | 12/2008 |
| WO | WO 2009155115 | A2 | 12/2009 |
| WO | WO 2009155115 | A3 | 12/2009 |
| WO | WO 2010022353 | A1 | 2/2010 |

OTHER PUBLICATIONS

Nobile et al. (Journal of Food Engineering, 2008; 89:57-63).*
Parris et al. (J. Agric. Food Chem. 2005;53:4788-4792).*
Article—Auvergne et al., "Reactivity of Wheat Gluten Protein during Mechanical Mixing: Radical and Nucleophilic Reactions for the Addition of Molecules on Sulfur," *Biomacromolecules*, vol. 9, No. 2, 2008, pp. 664-671.
Article—Camire, Mary Ellen, "Protein Functionality Modification by Extrusion Cooking," *JAOCS*, vol. 68, No. 3, Mar. 1991, pp. 200-205 (Presented at the 81st AOCS Annual Meeting, Baltimore, 1990).
Article—Hu et al., "Evaluation of the environmental fate of thymol and phenethyl Propionate in the laboratory," *Pest Management Science*, vol. 64, Issue 7, Jul. 2008, pp. 775-779.
Article—Kurniawan et al., "Chemical Modification of Wheat Protein-Based Natural Polymers: Grafting and Cross-Linking Reactions with Poly(ethylene oxide) Diglycidyi Ether and Ethyl Diamine," *Biomacromolecules*, vol. 8, No. 9, 2007, pp. 2909-2915.
Article—Lawton et al, "High-Temperature Short-Time Extrusion of Wheat Gluten and a Bran-Like Fraction," *Cereal Chem.*, vol. 62, No. 4, 1985, pp. 267-271.
Article—Liu at al., "Modifications of Soy Protein Plastic with Functional Monomer with Reactive Extrusion," *J. Polym. Environ.*, vol. 16, No. 3, 2008, pp. 177-182.
Article—Mastromatteo et al., "Controlled release of thymol from zein based film," *Innovative Food Science and Emerging Technologies*, vol. 10, 2009, pp. 222-227.
Article—Nobile et al., "Active packaging by extrusion processing of recyclable and biodegradable polymers," *Journal of Food Engineering*, vol. 93, 2009, pp. 1-6.
Article—Nobile et al., "Antimicrobial efficacy and release kinetics of thymol from zein films," *Journal of Food Engineering*, vol. 89, 2008, pp. 57-63.
Article—O'Lenick, Jr., Anthony J., "Silicone Emulsions and Surfactants—A Review," *Silicone Spectator*, May 2000, 18 pages.
Article—Parris, et al., "Encapsulation of Essential Oils in Zein Nanospherical Particles," *J. Agric. Food Chem.*, vol. 53, No. 12, Jun. 15, 2005, pp. 4788-4792.
Article—Redl et al., "Extrusion of Wheat Gluten Plasticized with Glycerol: Influence of Process Conditions on Flow Behavior, Rheological Properties, and Molecular Size Distribution," *Cereal Chem.*, vol. 76, No. 3, 1999, pp. 361-370.
Article—Sanchez-Garcia et al., "Novel Polycaprolactone Nanocomposites Containing Thymol of Interest in Antimicrobial Film and Coating Applications," *Journal of Plastic Film and Sheeting*, vol. 24, Jul.-Oct. 2008, pp. 239-251.
Article—Ullsten et al, "Enlarged Processing Window of Plasticized Wheat Gluten Using Salicylic Acid," *Biomacromolecules*, vol. 7, No. 3, 2006, pp. 771-776.
Article—Vaz et al., "Soy Matrix Drug Delivery Systems Obtained by Melt-Processing Techniques," *Biomacromolecules*, vol. 4, No. 6, Nov./Dec. 2003, pp. 1520-1529.
Article—Verbeek et al., "Extrusion Processing and Properties of Protein-Based Thermoplastics," *Macromolecular Materials and Engineering*, vol. 295, 2010, pp. 10-21.
Paper entitled "Chemistry of Crosslinking" from Thermo Fisher Scientific, Inc., 2010, 8 pages.
Presentation to the Midwest Chapter of the Society of Cosmetic Chemists—The HLB System—A Time Saving Guide to Surfactant Selection, Mar. 9, 2004, by Uniqema, 39 pages.
ASTM D 445-04—Standard Test Method for Kinematic Viscosity of Transparent and Opaque Liquids (and the Calculation of Dynamic Viscosity), Current edition approved May 1, 2004, originally approved in 1937.
ASTM 5034 95—Standard Test Method for Breaking Strength and Elongation of Textile Fabrics (Grab Test), Current edition approved May 15, 1995.
Search Report and Written Opinion for PCT/IB2011/054839 dated Jun. 26, 2012, 11 pages.

* cited by examiner

PROTEIN STABILIZED ANTIMICROBIAL COMPOSITION FORMED BY MELT PROCESSING

RELATED APPLICATIONS

The present application is a divisional of U.S. application Ser. No. 12/961,634, filed on Dec. 7, 2010, which is incorporated herein in its entirety by reference thereto.

BACKGROUND OF THE INVENTION

Certain types of botanical oils, such as thymol and carvacrol, are known to be environmentally friendly and effective in combating microorganisms. Unfortunately, however, the use of such oils has been limited in many commercial applications (e.g., wipes) due to their high volatility and instability in the presence of oxygen. Attempts to overcome this problem often involve the use of a larger amount of the botanical oils to prolong antimicrobial activity. Regrettably, this just leads to another problem in that high concentrations of essential oils can cause damage to certain types of food products, such as fruit. Other attempts have involved the encapsulation of the oil component with certain types of polymers, such as proteins. For example, an article entitled "*Encapsulation of Essential Oils in Zein Nanospherical Particles*" (Parris, et al., *J. Agric. Food Chem.* 2005, 53, 4788-4792) broadly describes the encapsulation of thymol in zein nanospheres by mixing the oil with zein particles in the presence of a solvent (e.g., ethanol). The particles are said to be useful for oral or injectable administration of biological materials into the body. Another article entitled "*Controlled Release of Thymol from Zein Based Film*" (Mastromatteo, et al., *J. Innovative Food and Emerging Technologies* 2009, 10, 222-227) broadly describes films formed by dissolving corn zein and glycerol into ethanol, and thereafter adding thymol to form a solution. The solution is poured into a Petri dish and dried to form the film.

One problem with the techniques described above is that they generally rely on solvents (e.g., ethanol) to help dissolve the botanical oil into a solution. A disadvantage of the use of solvents is that both the botanical oil and protein must be soluble in a common solvent system, which puts a limit on what type of components may be employed in the composition. Also, solvent-based solutions require a substantial amount of time, energy, and material for processing. Still further, a portion of the botanical oil may escape from the solution when the solvent is evaporated, which requires the use of a greater amount of the oil than would normally be needed. Notwithstanding the above, the ability to use a "solventless" process is complicated by the tendency of proteins to lose their flow properties when exposed to the intense shear and elevated temperature normally associated with melt processing. For example, proteins may undergo a conformational change ("denaturation") that causes disulfide bonds in the polypeptide to dissociate into sulfhydryl groups or thiyl radicals. Sulfhydryl groups form when disulfide bonds are chemically reduced while mechanical scission of disulfide bonds causes thiyl radicals to form. Once dissociated, however, free sulfhydryl groups randomly re-associate with other sulfhydryl groups to form new disulfide bond between polypeptides. Thiyl radicals can also randomly re-associate with other thiyl radicals forming new disulfide bonds or thiyl radicals can react with other amino acid functionality creating new forms of cross-linking between polypeptides. Because one polypeptide contains multiple thiol groups, random cross-linking between polypeptide leads to formation of an "aggregated" polypeptide network, which is relatively brittle and leads to a loss of flow properties.

As such, a need currently exists for a solventless process for forming a stable composition that contains an antimicrobially active botanical oil.

SUMMARY OF THE INVENTION

In accordance with one embodiment of the present invention, a method for forming an antimicrobial composition is disclosed that comprises dispersively blending a botanical oil, protein, and carrier fluid within a melt blending device at a temperature of from about 20° C. to about 100° C. and a shear rate of from about 1 to about 100 Pascal-seconds. Botanical oils constitute from about 0.1 wt. % to about 30 wt. % of the composition, proteins constitute from about 30 wt. % to about 95 wt. % of the composition, and carrier fluids constitute from about 1 wt. % to about 50 wt. % of the composition.

In accordance with another embodiment of the present invention, a melt-processed antimicrobial composition is disclosed that comprises at least one monoterpene phenol in an amount of from about 0.1 wt. % to about 30 wt. %, at least one melt-processible plant protein in an amount of from about 30 wt. % to about 95 wt. %, and at least one carrier fluid in amount of from about 1 wt. % to about 50 wt. %. In yet another embodiment, a method for removing bacteria from a surface is disclosed that comprises contacting the surface with a wipe that comprises a fibrous material that contains the melt-processed antimicrobial composition.

Other features and aspects of the present invention are discussed in greater detail below.

BRIEF DESCRIPTION OF THE FIGURES

A full and enabling disclosure of the present invention, including the best mode thereof, directed to one of ordinary skill in the art, is set forth more particularly in the remainder of the specification, which makes reference to the appended figures in which.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a 
still further embodiment. Thus, it is intended that the present invention covers such modifications and variations as come within the scope of the appended claims and their equivalents.

Generally speaking, the present invention is directed to a method for forming an antimicrobial composition that includes mixing an antimicrobially active botanical oil (e.g., thymol, carvacrol, etc.) and protein within a melt blending device (e.g., extruder). Despite the problems normally associated with melt processing proteins, the present inventors have discovered that the processing conditions and components may be selectively controlled to allow for the formation of a stable, melt-processed composition that is able to exhibit good mechanical properties. For example, the extrusion temperature(s) and shear rate employed during melt blending are relatively low to help limit polypeptide dissociation, thereby minimizing the impact of aggregation and embrittlement. While the use of such low temperature/shear conditions often tend to reduce mixing efficiency, the present inventors have discovered that a carrier fluid may be employed to enhance the ability of the botanical oil to flow into the internal structure of the protein where it can be retained in a stable manner. The composition is also typically anhydrous and generally free of solvents. In this manner, the protein will not generally disperse before use and prematurely release the botanical oil.

Various embodiments of the present invention will now be described in more detail below.

I. Components

A. Botanical Oil

Botanical oils are employed in the composition of the present invention as antimicrobial actives. The oil may be an "essential" oil that is extracted from a plant. Likewise, the botanical oil may also be isolated or purified from an essential oil, or it may simply be made synthetically to mimic a compound derived from a plant (e.g., synthetically made thymol). The botanical oils are generally soluble in lipids and believed to exhibit antimicrobial efficacy due to their ability to cause damage to the lipid component of the cell membrane in microorganisms, thereby inhibiting their proliferation. Essential oils are derived from herbs, flowers, trees, and other plants, and are typically present as tiny droplets between the cells of the plants and may be extracted by methods known to those of skill in the art (e.g., steam distillation, enfleurage (i.e., extraction using fat(s)), maceration, solvent extraction, or mechanical pressing). Examples of suitable essential oils for use in the present invention may include, for instance, anise oil, lemon oil, orange oil, oregano, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea *origanum* oil, *Hydastis carradensis* oil, *Berberidaceae daceae* oil, Ratanhiae and *Curcuma longa* oil, sesame oil, *macadamia* nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Still other essential oils known to those of skill in the art are also contemplated as being useful within the context of the present invention (e.g., International Cosmetic Ingredient Dictionary, $10^{th}$ and $12^{th}$ editions, 2004 and 2008, respectively, which are incorporated by reference).

In one embodiment, carvacrol and thymol-containing oils are purified from the species *Origanum vulgare* of a hirtum variety. Ideally this is a hybrid strain that produces high quality oils, but is not limited to this genus, species or strain. The oil extract may also be obtained from a plant of the genus *Nepeta* including, but not limited to species *Nepeta racemosa* (catmint), *Nepeta citriodora, Nepeta elliptica, Nepeta hindostoma, Nepeta lanceolata, Nepeta leucophylla, Nepeta longiobracteata, Nepeta mussinii, Nepeta nepetella, Nepeta sibthorpii, Nepeta subsessilis, Nepeta tuberosa, Thymus glandulosus, Thymus hyemalis, Thymus vulgaris* and *Thymus zygis*.

As indicated above, isolates and/or derivatives of essential oils may also be employed in the present invention. For example, monoterpene phenols are particularly suitable for use in the present invention, which may be isolated and purified from plant oil extracts, or made synthetically by known methods. Suitable monoterpene phenols may include, for instance, thymol, carvacrol, eucalyptol, etc. Thymol (isopropyl-cresol) is one particularly suitable monoterpene phenol, which is a crystalline substance that has a boiling point of about 238° C. at atmospheric pressure. Carvacrol (isopropyl-o-cresol), an isomer of thymol, is another suitable compound. Carvacrol is a liquid with a boiling point of about 233° C. at atmospheric pressure. Thymol and carvacrol, as well as isomers thereof, may be derived from plant oil extracts or synthesized. For example, carvacrol may be synthesized by the reaction of nitrous acid with 1-methyl-2-amino-4-propyl benzene. In addition to being employed in an isolated or pre-synthesized form, essential oils containing the monoterpene phenols as major constituents may be employed, with the final concentrations of the monoterpene phenols being within the ranges provided herein. The term "major constituent" generally refers to those essential oils having monoterpene phenols in an amount of more than 50 wt. %. It is well-known in the art that such essential oils may also contain lesser amounts of other constituents, such as non-aromatic terpene compounds. Essential oils with organic phenolic compounds as the major constituent include, for example, anise oil, bay oil terpineless, clove bud, clove leaf, clove oil, clove stem, *origanum* oil, Peru balsam, pimento oil, eucalyptus oil, and thyme oil.

Due to the stability achieved by the antimicrobial composition of the present invention, a relatively small amount of botanical oils may be employed and still achieve the desired antimicrobial efficacy. More particularly, the composition may employ botanical oils in an amount of from about 0.1 wt. % to about 30 wt. %, in some embodiments from about 0.5 wt. % to about 20 wt. %, and in some embodiments, from about 1 wt. % to about 10 wt. %.

B. Protein

The antimicrobial composition of the present invention also contains a protein. Because the botanical oil tends to leach out during storage and before it is used in the desired application, the protein helps enhance the long term stability of the oil and, in turn, antimicrobial efficacy. Without intending to be limited by theory, it is believed that the physical structure of the protein can effectively encapsulate the botanical oil and inhibit its premature release. Nevertheless, when it is desired to release the botanical oil prior to and/or during use, the protein can disperse (e.g., disintegrate, dissolve, change physical form, etc.) when placed in an aqueous environment. The amount of time needed for dispersal of the protein so that it releases the desired antimicrobial active will depend at least in part upon the particular end-use design criteria. In most embodiments, the protein will begin to disperse and release the antimicrobial active within about 5 minutes, suitably within about 1 minute, more suitably within about 30 seconds, and most suitably within about 10 seconds.

Examples of suitable proteins include vegetable proteins, dairy proteins, animal proteins, as well as concentrates or isolates thereof. The protein source may be, for instance, milk (e.g., casein or caeseinates), whey, corn (e.g., zein), wheat (e.g., wheat gluten), soy, or other vegetable or animal sources. Plant proteins are particularly suitable for use in the present invention, such as zein, corn gluten, wheat gluten, whey protein, soy protein, etc. Any form of protein may be used, such as isolates, concentrates and flour. For example, soy proteins may be in the form of an isolate containing from about 75 wt. % to about 98 wt. % protein, a concentrate containing from about 50 wt. % to about 75 wt. % protein, or flour containing from about 30 wt. % to about 50 wt. % protein. In certain embodiments, it is desirable to use a protein that is relatively pure, such as those having a protein content of about 75 wt. % or more, and in some cases, about 85 wt. % or more. Gluten proteins, for instance, may be purified by washing away any associated starch to leave a composite of gliadin and glutenin proteins. In one particular embodiment, a vital wheat gluten is employed. Such vital wheat gluten is commercially available as a creamy-tan powder produced from wheat flour by drying freshly washed gluten. For instance, vital wheat gluten can be obtained from Archer Daniels Midland ("ADM") of Decatur, Ill. under the designations WhetPro® 75 or 80. Similarly, purified soy protein isolates may be prepared by alkaline extraction of a defatted meal and acid precipitation, a technique well-known and used routinely in the art. Such purified soy proteins are commercially available from ADM under the designation PRO-FAM®, which typically have a protein content of 90 wt. % or more. Other purified soy protein products are also available from DuPont of Louisville, Ky. under the designation PRO-COTE® and from Central Soya under the designation Promie R.

If desired, the protein may also be modified using techniques known in the art to improve its ability to disperse in an aqueous solution, which may be applied to the composition to release the botanical oil during and/or just prior to use as described in more detail below. Suitable modification techniques may include pH modification, denaturation, hydrolysis, acylation, reduction, oxidation, etc. Just as an example, gluten may sometimes absorb water until it begins to repel excess water. This results in gluten molecules that are associated closely together such that they resist dispersion in aqueous solutions. To counteract this tendency, the protein may be treated with a pH modifier to increase its solubility in aqueous environments. Typically, the pH modifier is a basic reagent that can raise the pH of the protein, thereby causing it to become more soluble in aqueous solutions. Monovalent cation-containing basic reagents (hereafter "monovalent basic reagents") are particularly suitable for use in the present invention. Examples of such monovalent basic reagents include, for instance, alkali metal hydroxides (e.g., sodium hydroxide, ammonium hydroxide, etc.), ammonia, etc. Of course, multivalent reagents, such as alkaline metal hydroxides (e.g., calcium hydroxide) and alkaline metal oxides (e.g., calcium oxide), may also be employed if desired. When employed, the pH modifier may be present in an amount such that the pH of the protein is from about 7 to about 14, and in some embodiments, from about 8 to about 12.

Hydrolysis of the protein material may also improve water solubility, and can be effected by treating the protein with a hydrolytic enzyme. Many enzymes are known in the art which hydrolyze protein materials, including, but not limited to, proteases, pectinases, lactases, and chymotrypsin. Enzyme hydrolysis is effected by adding a sufficient amount of enzyme to an aqueous dispersion of protein material, typically from about 0.1% to about 10% enzyme by weight of the protein material, and treating the enzyme and protein dispersion. After sufficient hydrolysis has occurred the enzyme may be deactivated by heating, and the protein material may be precipitated from the solution by adjusting the pH of the solution to about the isoelectric point of the protein material.

The antimicrobial composition of the present invention typically employs proteins in an amount of from about 30 wt. % to about 95 wt. %, in some embodiments from about 40 wt. % to about 90 wt. %, and in some embodiments, from about 50 wt. % to about 80 wt. %.

C. Carrier Fluid

A carrier fluid may also be employed in the antimicrobial composition to help render the protein more flowable under melt processing conditions and able to receive the botanical oil within its internal structure. Suitable carrier fluids may include, for instance, polyhydric alcohols, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), etc. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable carrier fluids may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic carboxylic acids may also be used, such as lactic acid, maleic acid, acrylic acid, copolymers of ethylene and acrylic acid, polyethylene grafted with maleic acid, polybutadiene-co-acrylic acid, polybutadiene-co-maleic acid, polypropylene-co-acrylic acid, polypropylene-co-maleic acid, and other hydrocarbon based acids. A low molecular weight carrier fluid is preferred, such as less than about 20,000 g/mol, preferably less than about 5,000 g/mol and more preferably less than about 1,000 g/mol.

If desired, the carrier fluid may be selected to have a certain pH (refers to the pH prior to incorporation into the antimicrobial composition). For example, carrier fluids having a relatively low pH can reduce the tendency of gluten proteins to aggregate during melt processing. Thus, when gluten proteins are employed, a carrier fluid may be selected that has a pH of about 6 or less, in some embodiments from about 1 to about 5, and in some embodiments, from about 2 to about 4. Examples of such carrier fluids may include aliphatic carboxylic acids, such as lactic acid, maleic acid, acrylic acid, etc. In other embodiments, it may be desirable to use carrier fluids having a higher pH, such as when the plant protein is not generally sensitive to pH. For example, soy proteins generally lack the cysteine residues that lead to aggregation in gluten proteins. Thus, when employed, the soy protein may be used with carrier fluids having a relatively wide range of pH levels. One example of such a carrier fluid is glycerol, which has a pH of about 6.

The amount of the carrier fluids employed depends in part on the nature of the selected botanical oil and protein, but is typically from about 1 wt. % to about 50 wt. %, in some embodiments from about 5 wt. % to about 30 wt. %, and in some embodiments, from about 10 wt. % to about 20 wt. %.

D. Other Components

In addition to those noted above, still other additives may also be incorporated into the composition. For example, starch polymers, which are often found in commercially available protein compositions, may also be employed in the present invention. When employed, such starch polymers typically constitute from about 1 wt. % to about 50 wt. % of the composition, in some embodiments from about 10 wt. % to about 45 wt. %, and in some embodiments, from about 20 wt. % to about 40 wt. % of the composition.

Although starch polymers are produced in many plants, typical sources includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm. Chemically modified starches may also be employed as they typically possess a higher degree of water sensitivity, and therefore can help facilitate water sensitivity during use. Such chemically modified starches may be obtained through typical processes known in the art (e.g., esterification, etherification, oxidation, acid hydrolysis, enzymatic hydrolysis, etc.). Starch ethers and/or esters may be particularly desirable, such as hydroxyalkyl starches, carboxymethyl starches, etc. The hydroxyalkyl group of hydroxyalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch. The starch polymer may contain different weight percentages of amylose and amylopectin, different polymer molecular weights, etc. High amylose starches contain greater than about 50% by weight amylose and low amylose starches contain less than about 50% by weight amylose. Although not required, low amylose starches having an amylose content of from about 10% to about 40% by weight, and in some embodiments, from about 15% to about 35% by weight, are particularly suitable for use in the present invention. Examples of such low amylose starches include corn starch and potato starch, both of which have an amylose content of approximately 20% by weight.

Dispersion aids may also be employed to help create a uniform dispersion of the oil/protein/carrier fluid and retard or prevent separation of the antimicrobial composition into constituent phases. When employed, the dispersion aid(s) typically constitute from about 0.01 wt. % to about 10 wt. %, in some embodiments from about 0.1 wt. % to about 5 wt. %, and in some embodiments, from about 0.5 wt. % to about 4 wt. % of the antimicrobial composition. Although any dispersion aid may generally be employed in the present invention, surfactants having a certain hydrophilic/lipophilic balance may improve the long-term stability of the composition. As is known in the art, the relative hydrophilicity or lipophilicity of an emulsifier can be characterized by the hydrophilic/lipophilic balance ("HLB") scale, which measures the balance between the hydrophilic and lipophilic solution tendencies of a compound. The HLB scale ranges from 0.5 to approximately 20, with the lower numbers representing highly lipophilic tendencies and the higher numbers representing highly hydrophilic tendencies. In some embodiments of the present invention, the HLB value of the surfactants is from about 1 to about 15, in some embodiments from about 1 to about 12 and in some embodiments, from about 2 to about 10. If desired, two or more surfactants may be employed that have HLB values either below or above the desired value, but together have an average HLB value within the desired range.

One particularly suitable class of surfactants for use in the present invention are nonionic surfactants, which typically have a hydrophobic base (e.g., long chain alkyl group or an alkylated aryl group) and a hydrophilic chain (e.g., chain containing ethoxy and/or propoxy moieties). For instance, some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. In one particular embodiment, the nonionic surfactant may be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters may be saturated or unsaturated, substituted or unsubstituted, and may contain from 6 to 22 carbon atoms, in some embodiments from 8 to 18 carbon atoms, and in some embodiments, from 12 to 14 carbon atoms. In one particular embodiment, mono- and di-glycerides of fatty acids may be employed in the present invention.

The composition may also contain a preservative or preservative system to inhibit the growth of microorganisms over an extended period of time. Suitable preservatives may include, for instance, alkanols, disodium EDTA (ethylenediamine tetraacetate), EDTA salts, EDTA fatty acid conjugates, isothiazolinone, benzoic esters (parabens) (e.g., methylparaben, propylparaben, butylparaben, ethylparaben, isopropylparaben, isobutylparaben, benzylparaben, sodium methylparaben, and sodium propylparaben), benzoic acid, propylene glycols, sorbates, urea derivatives (e.g., diazolindinyl urea), and so forth. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate). Another suitable preservative is Kathon CG®, which is a mixture of methylchloroisothiazolinone and methylisothiazolinone available from Rohm & Haas; Mackstat H 66 (available from McIntyre Group, Chicago, Ill.). Still another suitable preservative system is a combination of 56% propylene glycol, 30% diazolidinyl urea, 11% methylparaben, and 3% propylparaben available under the name GERMABEN® II from International Specialty Products of Wayne, N.J.

To better enhance the benefits to consumers, other optional ingredients may also be used. For instance, some classes of ingredients that may be used include, but are not limited to: antioxidants (product integrity); anti-reddening agents, such as aloe extract; astringents-cosmetic (induce a tightening or tingling sensation on skin); colorants (impart color to the product); deodorants (reduce or eliminate unpleasant odor and protect against the formation of malodor on body surfaces); fragrances (consumer appeal); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); and thickeners (to increase viscosity).

While a wide variety of different components may be employed, it is typically desired that the antimicrobial composition is formed without the use of solvents, particularly organic solvents, such as organic alcohols (e.g., ethanol). Not only does this enhance manufacturing efficiency, but it also limits the evaporation of the botanical oil that might otherwise be encountered during removal of the solvent. While the composition may be generally free of such solvents, it should of course be understood that a small amount may still be present in the resulting composition. Regardless, the composition typically contains solvents in an amount less than about 20 wt. %, in some embodiments less than about 10 wt. %, and in some embodiments, from about 0.01 wt. % to about 5 wt. %.

II. Melt Processing Technique

As indicated above, the antimicrobial composition of the present invention is formed by processing the components together in a melt blending device (e.g., extruder). The mechanical shear and heat provided by the device allows the components to be blended together in a highly efficient manner without the use of a solvent. Batch and/or continuous melt blending techniques may be employed in the present invention. For example, a mixer/kneader, Banbury mixer, Farrel continuous mixer, single-screw extruder, twin-screw extruder, roll mill, etc., may be utilized. One particularly suitable melt-blending device is a co-rotating, twin-screw extruder (e.g., USALAB twin-screw extruder available from Thermo Electron Corporation of Stone, England or an extruder available from Werner-Pfleiderer from Coperion Ramsey, N.J.). The raw materials (e.g., botanical oil, protein, carrier fluid, etc.) may be supplied to the melt blending device separately and/or as a blend. For example, the protein and/or botanical oil may be initially fed to a feeding port of the twin-screw extruder. Thereafter, a carrier fluid may be injected into the extruder downstream from the botanical oil and protein. Alternatively, the components may be simultaneously fed to the feed throat of the extruder or separately at a different point along its length.

Regardless, the materials are dispersively blended under low shear/pressure and at a low temperature to minimize protein dissociation associated with aggregation. Nevertheless, the temperature is still typically slightly at or above the softening point of the protein. For example, melt blending typically occurs at a temperature of from about 20° C. to about 100° C., in some embodiments, from about 30° C. to about 80° C., and in some embodiments from about 40° C. to about 70° C. Likewise, the apparent shear rate during melt blending may range from about 100 seconds$^{-1}$ to about 5,000 seconds$^{-1}$, in some embodiments from about 200 seconds$^{-1}$ to about 2,000 seconds$^{-1}$, and in some embodiments, from about 400 seconds$^{-1}$ to about 1,200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows. The apparent melt viscosity of the resulting antimicrobial composition may be relatively low, such as from about 1 to about 100 Pascal seconds (Pa·s), in some embodiments from about 5 to about 60 Pa·s, and in some embodiments from about 20 to about 50 Pa·s, as determined at a temperature of 160° C. and a shear rate of 1000 sec$^{-1}$. The melt flow index (190° C., 2.16 kg) of the composition may also range from about 0.05 to about 50 grams per 10 minutes, in some embodiments from about 0.1 to about 15 grams per 10 minutes, and in some embodiments, from about 0.5 to about 5 grams per 10 minutes.

Once formed, the antimicrobial composition of the present invention may be used in a variety of forms, such as particles, lotion, cream, jelly, liniment, ointment, salve, oil, foam, gel, film, wash, coating, liquid, capsule, tablet, concentrate, etc. In one particular embodiment, for example, the antimicrobial composition may be formed into a film, either alone or in conjunction with an additional film-forming material. The film may be used in a wide variety of applications, such as in the packaging of items (e.g., food products, medical products, garments, garbage, absorbent articles (e.g., diapers), etc. The film may have a mono-layered or multi-layered structure. Multilayer films normally contain at least one base layer and at least one skin layer, but may contain any number of layers desired. The base layer and/or the skin layer may contain the antimicrobial composition of the present invention. Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes. In yet another embodiment, however, the film is formed using a casting technique.

Besides being formed into a film, the antimicrobial composition of the present invention may also be formed into particles and applied to other types of articles. Powderization may be accomplished using any of a variety of known techniques. Suitable pulverizing techniques may include, for instance, cryogenic disk mill or hammer mill, solid state shear pulverization using cold extrusion technology, double stream mills (e.g., Type PSKM or PPSM mills available from Pallmann Industries), and other known powderization methods. Cryogenic downsizing techniques or cold extrusion pulverization techniques may be particularly suitable as such techniques limit the degree to which the volatile botanical oil is heated and lost during powder formation. Examples of such techniques are described in more detail, for instance, in U.S. Pat. No. 5,395,055 to Shutov, et al., which is incorporated herein in its entirety by reference thereto for all purposes. The shape of the particles may vary as desired, such as spherical, nodular, flake, etc. The average size of the particles may also be selected to optimize the ability of the botanical oil to be released during use. More particularly, the present inventors have discovered that smaller particle sizes can generally result in a greater release rate of the oil when dispersed in an aqueous solution due to their high surface area to volume ratio. However, at too small of a size, the botanical oil may become unstable during storage and actually begin to leach out of the particles prior to use. In this regard, the present inventors have discovered that an average size of from about 10 to about 3,000 micrometers, in some embodiments from about 50 to about 800 micrometers, and in some embodiments, from about 100 to about 600 micrometers, can help achieve a good balance between stability and releasibility.

Regardless of its particular form, the antimicrobial particles may be applied to a wide variety of different articles for imparting antimicrobial efficacy. In one particular embodiment, the composition is applied to a wipe. Such wipes may be used to reduce microbial or viral populations on a hard surface (e.g., sink, table, counter, sign, and so forth) or surface on a user/patient (e.g., skin, mucosal membrane, such as in the mouth, nasal passage, stomach, vagina, etc., wound site, surgical site, and so forth). The wipe may provide an increased surface area to facilitate contact of the composition with microorganisms. In addition, the wipe may also serve other purposes, such as providing water absorption, barrier properties, etc. The wipe may also eliminate microorganisms through frictional forces imparted to the surface.

The wipe may be formed from any of a variety of materials as is well known in the art. Typically, however, the wipe includes a fibrous web that contains absorbent fibers. For example, the wipe may be a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter ("gsm"), in some embodiments less than about 80 gsm, in some embodiments less than about 60 grams per square meter, and in some embodiments, from about 10 to about 60 gsm. Any of a variety of materials can also be used to form the paper web(s) of the product. For example, the material used to make the paper product may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19". Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, bamboo, algae, and so forth. In addition, in some instances, synthetic fibers can also be utilized.

If desired, the absorbent fibers (e.g., pulp fibers) may be integrated with synthetic fibers to form a composite. Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; polyhydroxyalkanoate; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al., which is incorporated herein in its entirety by reference thereto for all purposes. The relative percentages of such fibers may vary over a wide range depending on the desired characteristics of the composite. For example, the composite may contain from about 1 wt. % to about 60 wt. %, in some embodiments from 5 wt. % to about 50 wt. %, and in some embodiments, from about 10 wt. % to about 40 wt. % synthetic polymeric fibers. The composite may likewise contain from about 40 wt. % to about 99 wt. %, in some embodiments from 50 wt. % to about 95 wt. %, and in some embodiments, from about 60 wt. % to about 90 wt. % absorbent fibers.

Composites, such as described above, may be formed using a variety of known techniques. For example, a nonwoven composite may be formed that is a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes. Alternatively, the nonwoven composite may be formed be formed by hydraulically entangling staple length fibers and/or filaments with high-pressure jet streams of water. Various techniques for hydraulically entangling fibers are generally are disclosed, for example, in U.S. Pat. No. 3,494,821 to Evans and U.S. Pat. No. 4,144,370 to Bouolton, which are incorporated herein in their entirety by reference thereto for all purposes. Hydraulically entangled nonwoven composites of continuous filaments (e.g., spunbond web) and natural fibers (e.g., pulp) are disclosed, for example, in U.S. Pat. No. 5,284,703 to Everhart, et al. and U.S. Pat. No. 6,315,864 to Anderson, et al., which are incorporated herein in their entirety by reference thereto for all purposes. Hydraulically entangled nonwoven composite of staple fiber blends (e.g., polyester and rayon) and natural fibers (e.g., pulp), also known as "spunlaced" fabrics, are described, for example, in U.S. Pat. No. 5,240,764 to Haid, et al., which is incorporated herein in its entirety by reference thereto for all purposes.

Regardless of the materials or processes utilized to form the wipe, the basis weight of the wipe is typically from about 20 to about 200 grams per square meter ("gsm"), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al., which are incorporated herein in their entirety by reference thereto for all purposes.

The composition may be incorporated into the wipe in a variety of different ways. For example, the composition may be applied to a surface of the wipe using known techniques, such as printing, dipping, spraying, melt extruding, coating (e.g., solvent coating, powder coating, brush coating, etc.), foaming, and so forth. If desired, the composition may be applied in a pattern that covers from about 5% to about 95%, in some embodiments from about 10% to about 90%, and in some embodiments, from about 20% to about 75% of a surface of the wipe. Such patterned application may have various benefits, including enhanced aesthetic appeal, improved absorbency, etc. The particular type or style of the pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. It should be appreciated that the "pattern" may take on virtually any desired appearance. The composition may also be blended with the fibers used to form the wipe. This may be particularly useful when the composition is in the form of particles. For example, such particles may be blended with the absorbent fibers (e.g., pulp fibers, staple fibers, etc.) during hydraulic entanglement, coforming, etc. The particles may also be incorporated into the thermoplastic material of the wipe (e.g., meltblown web) using known techniques.

The amount of the antimicrobial composition on the wipe may vary depending on the nature of the substrate and its intended application. For example, the add-on level of the composition may be from about 5% to about 100%, in some embodiments from about 10% to about 80%, and in some embodiments, from about 20% to about 70%. The "add-on level" is determined by subtracting the weight of the untreated substrate from the weight of the treated substrate, dividing this calculated weight by the weight of the untreated substrate, and then multiplying by 100%. Lower add-on levels may provide optimum functionality of the substrate, while higher add-on levels may provide optimum antimicrobial efficacy.

To use the composition, an aqueous solution may simply be added, thereby dispersing the protein and releasing the botanical oil. The aqueous solution may contain only water, or it may contain water in combination with other components. For example, a weak acid may be employed to help disperse the protein and facilitate the release of the oil upon contact with the aqueous solution. Suitable acids for this purpose may include, for instance, organic carboxylic acids, such as citric acid, oxalic acid, lactic acid, acetic acid, etc. Regardless, the present inventors have surprisingly discovered that the amount of the botanical oil released into the aqueous solution can be even greater than the normal solubility limit of the oil in water. Without intending to be limited by theory, it is believed that this can be achieved because the physical structure of the protein is able to effectively "carry" the volatile into the released solution. For example, the solubility limit of thymol in water (at 25° C.) is typically about 0.1 wt. %. When released from the composition of the present invention, however, the concentration of thymol in the released solution can be greater than 0.1 wt. %, in some embodiments greater than about 0.5 wt. %, in some embodiments from about 1 wt. % to about 10 wt. %, and in some embodiments, from about 2 wt. % to about 8 wt. %.

The present inventors have discovered that the composition of the present invention may inhibit (e.g., reduce by a measurable amount or to prevent entirely) the growth of one or more microorganisms when exposed thereof. Examples of microorganisms that may be inhibited include bacteria, protozoa, algae, and fungi (e.g., molds and yeast). Furthermore is possible to use this invention to inactivate viruses, prions and other infectious particles. For example, the composition may inhibit the growth of several medically significant bacteria groups, such as Gram negative rods (e.g., Entereobacteria); Gram negative curved rods (e.g., *Heliobacter, Campylobacter*, etc.); Gram negative cocci (e.g., *Neisseria*); Gram positive rods (e.g., *Bacillus, Clostridium*, etc.); Gram positive cocci (e.g., *Staphylococcus, Streptococcus*, etc.); obligate intracellular parasites (e.g., *Ricckettsia* and *Chlamydia*); acid fast rods (e.g., *Myobacterium, Nocardia*, etc.); spirochetes (e.g., *Treponema, Borellia*, etc.); and mycoplasmas (i.e., tiny bacteria that lack a cell wall). Particularly species of bacteria that may be inhibited with the composition of the present invention include *Escherichia coli* (Gram negative rod), *Klebsiella pneumonia* (Gram negative rod), *Streptococcus* (Gram positive cocci), *Salmonella choleraesuis* (Gram negative rod), *Staphyloccus aureus* (Gram positive cocci), and *P. aeruginosa* (Gram negative rod). In addition to bacteria, other microorganisms of interest include fungi (e.g., *Aspergillus niger*) and yeasts (e.g., *Candida albicans*).

Upon exposure for a certain period of time, the composition may provide a log reduction of at least about 2, in some embodiments at least about 3, in some embodiments at least about 4, and in some embodiments, at least about 5 (e.g., about 6). Log reduction, for example, may be determined from the % population killed by the composition according to the following correlations:

| % Reduction | Log Reduction |
| --- | --- |
| 90 | 1 |
| 99 | 2 |
| 99.9 | 3 |
| 99.99 | 4 |
| 99.999 | 5 |
| 99.9999 | 6 |

Such a log reduction may be achieved in accordance with the present invention after only a relatively short exposure time. For example, the desired log reduction may be achieved after exposure for only 30 minutes, in some embodiments 15 minutes, in some embodiments 10 minutes, in some embodiments 5 minutes, in some embodiments 1 minute, and in some embodiments, 30 seconds.

The present invention may be better understood with reference to the following examples.

Materials Employed

Thymol (99.5% purity) was obtained from Sigma-Aldrich.
Carvacrol (98% purity) was obtained from Sigma-Aldrich.
Eucalyptol (C80601) was obtained from Sigma-Aldrich.

Soy Protein Flour (50% protein, 50% starch) was obtained from ADM.
WhetPro® 75 vital wheat gluten (75% protein, 25% starch) was obtained from ADM.
Emery 917 Glycerine (or Glycerol) was obtained from Cognis Oleochemicals.
L-Lactic Acid (Purac)

Test Methods

Thymol Stability

Samples were placed in an oven at 40° C., 50° C., or 55° C. for a certain number of days. The residual thymol level was determined through "High Performance Liquid Chromatography (HPLC) analysis." More particularly, the thymol level in each sample was determined by generating a thymol calibration curve by the following method. Approximately 70 mg thymol was weighed into a 100-mL volumetric flask. Approximately 50-mL of a 0.1% acetic acid:IPA mixture (50:50) was added to the flask and the contents swirled to promote dissolution. The volume was diluted with a 0.1% acetic acid:IPA mixture (50:50) and subsequent dilutions were performed to generate a calibration curve with a concentration range of approximately 700 µg/mL to 70 µg/mL. Samples were prepared as follows. Approximately 100 mg of sample was used for each code, where each code was analyzed in duplicate at every pull point. The measured material was cut up into small pieces and placed into a 40-mL vial. To each vial, 10.0 mL 0.1% acetic acid was added and the contents were shaken and sonicated for 30 minutes periods until the sample is dispersed. To each vial, 10.0 mL IPA was added and the contents were sonicated for 10 minutes to promote mixing and extraction of thymol. The resulting solutions were filtered through nylon filters prior to injection. Thymol levels were calculated using the thymol calibration curve described above.

HPLC Equipment & Conditions
Column: Phenomenex $NH_2$
Column Temperature Ambient
Mobile Phase: 50:50 (IPA:0.1% acetic acid)
Flow rate: 0.6 mL/min.
Injection volume: 15 microliters
ELS detection: 280 nm Thymol Concentrations in Extractions An aliquot of a sample was centrifuged at approximately 5000 rpm until visible settling occurred (approximately 30 minutes). The solution was filtered using two (2) different types of syringe filters: (1) Pall Life Acrodisc 13 mm 0.2 micron nylon membrane and (2) Whatman Puradisc-0.2 micron polyethersulfone membrane with polypropylene housing. 1.0 mL of the centrifuged solution was pipetted into a 10-mL flask. The contents were dissolved and diluted with a 0.1% AA:IPA (50:50) solution to volume. The solution was then filtered with Pall Acrodisc 0.45 micron nylon membrane. The thymol concentration was determined through "High Performance Liquid Chromatography (HPLC) analysis" according to the following conditions:

HPLC Equipment & Conditions
HPLC: Agilent 1100 HPLC system.
Column: Phenomenex Luna $NH_2$ (5 µm, 250 mm×4.6 mm)-ambient
Detector: UV/Vis at 280 nm
Mobile Phases: (75:25) (IPA: 0.1% acetic acid)
Flow Rate: approximately 0.6 mL/min.
Injection Volume: approximately 15 µL
Run Time: 6 minutes
Zone of Inhibition To determine antimicrobial efficacy, a zone of inhibition test was performed. More specifically, a 0.05 g sample was placed on a freshly spreading lawn of test microorganism on TSA (Trypticase Soy Agar). Two microorganisms were used, *Staphylococcus aureus* (ATCC #27660) as a Gram positive bacteria and *Escherichia coli* as a Gram negative bacteria (ATCC #25922). After 24 hours incubation at 37° C., plates were measured for clear zones of inhibition surrounding each sample (Clear zone (mm)=diameter of clear zone−sample (wipe) diameter).

Microplate Assay

To determine the germicidal efficacy of an extracted thymol solution, a microplate germicidal assay was performed. In this method, the test solution was brought into contact with 60 wells of test microorganisms (4*$10^6$ CFU (colony forming unit)/well) coated on the bottom of 96 well flat plates for 4½ minutes. At the end of the contact time, 200 µL of a "Letheen" neutralizing broth (included 0.5% Tween 80) was added to each well to deactivate the active ingredients. After addition of the neutralizer, 50 µL of TSB (Tryptic Soy Broth) was added and then the microplate was incubated to allow for out-growth of survivors. After incubation, the number of wells showing growth of the target microorganism was recorded. If the media in the well was turbid, then the well was counted as a failure to disinfect. If the well was not turbid after incubation, then the well was recorded as achieving disinfection. All tests were performed against two different microorganisms, *Staphylococcus aureus* (ATCC #6538) as Gram positive bacteria and *Pseudomonas aeruginosa* (ATCC #15442) as Gram negative bacteria.

EXAMPLE 1

A "PRISM USALAB 16" lab scale twin screw extruder was employed to melt process five (5) different samples of protein (WhetPro® 75 or soy flour), glycerol, and thymol. The extruder contained eleven (11) different zones, although zones 1 through 5 were not utilized in this Example. Temperature zone 11 was a strand die. The protein and thymol were pre-blended (6.6 wt % thymol and 93.4%) and subsequently added to the extruder at zone 6 at a feed rate of 0.5 lbs/hr. Glycerol was then added at zone 7 at a feed rate of 0.21 lb/hr. The screw configuration was composed of conveying elements at zones 6 and 7, kneading blocks at zones 8 and 9, and conveying elements at zone 10. The screw speed was 50 rpm. The resulting strand was pelletized to form a pellet with a size of about 3 mm in diameter. The temperature profile for each of the five (5) blend samples is set forth below.

| Sample | Protein Type | Target Temp. (° C.) | Temperature Profile (° C.) | | | | | |
|---|---|---|---|---|---|---|---|---|
| | | | Zone 6 | Zone 7 | Zone 8 | Zone 9 | Zone 10 | Zone 11 |
| 1 | Gluten | Ambient | 28 | 31 | 32 | 34 | 32 | 33 |
| 2 | Gluten | 50° C. | 27 | 31 | 34 | 40 | 50 | 41 |
| 3 | Gluten | 90° C. | 29 | 33 | 37 | 49 | 90 | 48 |
| 4 | Gluten | 120° C. | 35 | 42 | 51 | 68 | 120 | 67 |
| 5 | Soy flour | 90° C. | 25 | 28 | 31 | 42 | 90 | 61 |

After processing, it was determined that Samples 1-5 retained 90.8 wt. %, 88.2 wt. %, 88.4 wt. %, 85.4 wt. %, and 99.4 wt. %, respectively, of their initial thymol levels. Once formed, the samples were put into an air tight bag and placed in −10° C. freezer. The resulting samples were tested for thymol stability and zone of inhibition using the test methods described above. The results are set forth below in Tables 1 and 2.

TABLE 1

Thymol Level After Aging at 40° C.

| Sample | Thymol level (wt. %) | | | | | |
|---|---|---|---|---|---|---|
| | 1 day | 4 days | 10 days | 21 days | 39 days | 60 days |
| 1 | 4.07 | 3.75 | 4.09 | 3.83 | 3.69 | 3.44 |
| 2 | 4.04 | 3.95 | 3.78 | 3.91 | 4.37 | 3.97 |
| 3 | 4.42 | 4.4 | 4.14 | 4.37 | 3.99 | 3.88 |
| 4 | 4.16 | 4.49 | 4.57 | 4.72 | 4.52 | 3.99 |
| 5 | 4.21 | 4.51 | 4.42 | 4.2 | 4.27 | 4.58 |

TABLE 2

Zone of Inhibition Area After Aging at 40° C.

| Sample | Area of ZOI (mm) | | | | | | | | | | | | | |
|---|---|---|---|---|---|---|---|---|---|---|---|---|---|---|
| | 0 days | | 1 day | | 4 days | | 10 days | | 20 days | | 40 days | | 60 days | |
| | E. coli | S. aureus | E. coli | S. aureus | E. coli | S. aureus | E. coli | S. aureus | E. coli | S. aureus | E. coli | S. aureus | E. coli | S. aureus |
| 1 | 5 | 6 | 6 | 6 | 7 | 6 | 6 | 5 | 7 | 4 | 6 | 4 | 6 | 4 |
| 2 | 5 | 6 | 6 | 6 | 6 | 6 | 6 | 5 | 7 | 4 | 7 | 4 | 6 | 4 |
| 3 | 6 | 6 | 6 | 6 | 6 | 6 | 5 | 5 | 7 | 4 | 6 | 3 | 5 | 4 |
| 4 | 5 | 6 | 6 | 6 | 6 | 5 | 5 | 4 | 6 | 5 | 5 | 3 | 5 | 4 |
| 5 | 10 | 10 | 10 | 10 | 10 | 11 | 5 | 3 | 2 | 2 | 1.5 | 2.5 | 0 | 0 |

As indicated in Table 1, the thymol levels remained high even after approximately 60 days of aging at 40° C. Table 2 also reveals that after extrusion, thymol in Samples 1-4 still maintained antimicrobial activity, even after 60 days of aging at 40° C. Example 5 (soy flour at 120° C.) did not exhibit activity after 60 days, but was still effective after 40 days. Without intending to be limited by theory, it is believed that this difference may stem from the difference in protein concentrations between the WhetPro® 75 (75% protein) and the soy flour (50% protein).

Figure 1:
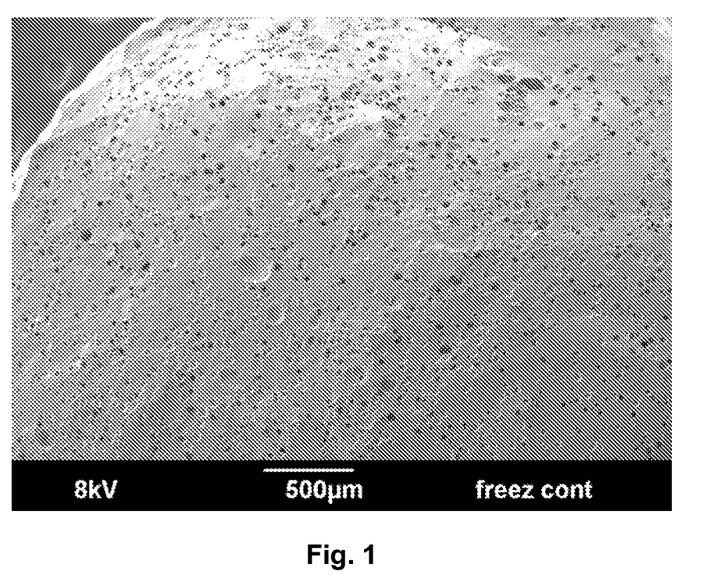
FIG. 1 is an SEM microphotograph of a control sample containing 70 wt. % gluten and 30 wt. % glycerol.
Figure 2:
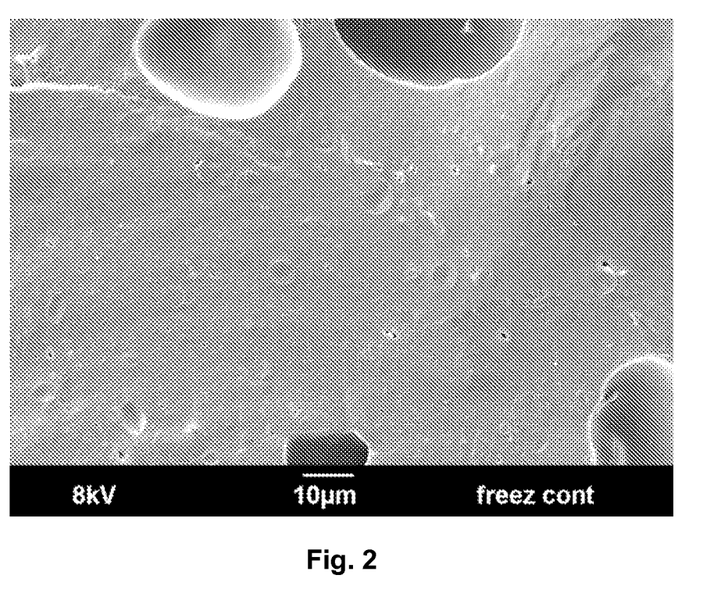
FIG. 2 is an SEM microphotograph of a control sample containing 70 wt. % gluten and 30 wt. % glycerol.
Figure 3:
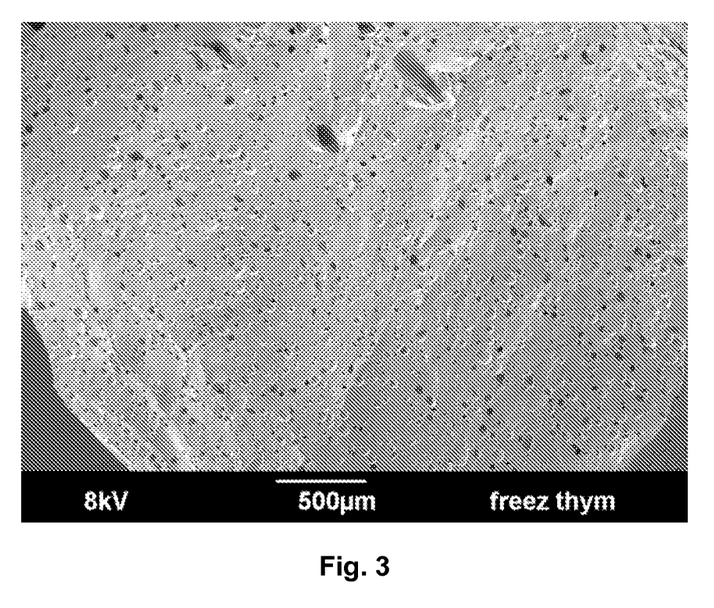
FIG. 3 is an SEM microphotograph of Sample 3 of Example 1.
Figure 4:
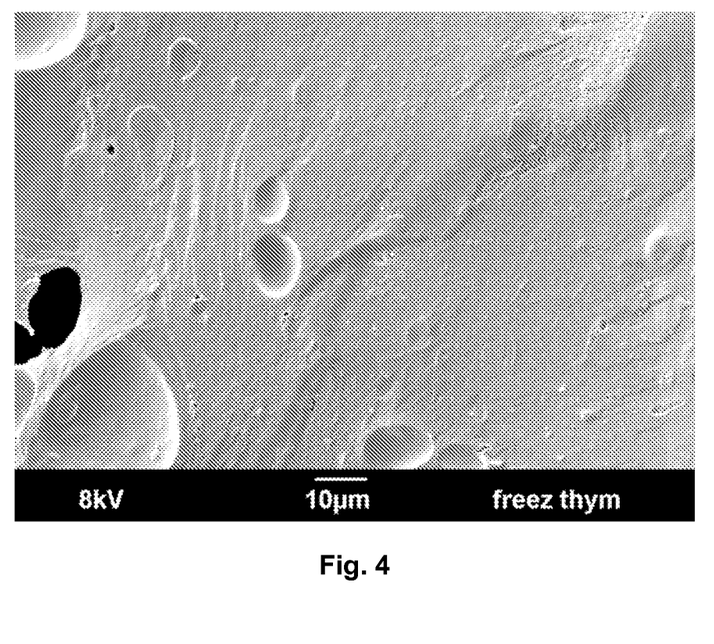
FIG. 4 is an SEM microphotograph of Sample 3 of Example 1.

SEM microphotographs were taken of Sample 3 and a control sample containing no thymol (70 wt. % gluten and 30 wt. % glycerol). The results are shown in FIGS. 1-4. As shown, there is no structural or morphological difference between the sample containing thymol (Sample 3, FIGS. 3-4) and the control sample (FIGS. 1-2). This indicates that thymol is homogenously compatible and retained within the protein structure. Also, there is no phase separation between the thymol and protein/glycerol matrix, which helps to providing for the prolonged release of the thymol.

EXAMPLE 2

WhetPro® 75 was placed in desiccant glass jar containing ammonium hydroxide solution (20-35% ammonia, 65-80% water) for 10 days. The mixture was then extruded with thymol at a concentration of 85 wt. % treated gluten and 15 wt. % thymol. Specifically, a PRISM USALAB 16" lab scale twin screw extruder was employed to melt process the ammonium hydroxide treated WhetPro® 75 and thymol. The extruder contained eleven (11) different zones, although zones 1 through 5, and 11 were not utilized in this Example. The extruder was used without the die system (zone 11) to allow for ease of material to exit extruder. The treated protein and thymol were pre-blended (17 wt % thymol and 83 wt. % protein) and subsequently added to the extruder at zone 6 at a feed rate of 0.4 lbs/hr. The screw configuration was composed of conveying elements at zones 6 and 7, kneading blocks at zones 8 and 9, and conveying elements at zone 10. The screw speed was 100 rpm. The temperature profile for zones 6-10 was 35° C., 44° C., 56° C., 70° C., 70° C. respectively.

The material was pelletized and cooled by placing in −32° C. for minimum of 24 hrs, resulting cooled material was powderized via Brickmann/Retsch lab scale grinding mill (set speed=1) and collected at a size of 250 to 425 μm by sieving. Sample was tested for thymol stability after aging at 50° C. for 1, 4, 15, and 18 days using the test methods described above. The results indicated that when gluten was treated with NH$_4$OH, the rate loss of thymol decreased by approximately one half (0.01% per hour) as compared to a control of untreated gluten (0.02% per hour).

EXAMPLE 3

A "PRISM USALAB 16" lab scale twin screw extruder was employed to melt process WhetPro® 75, lactic acid, and thymol. The extruder contained eleven (11) different zones, although zones 1 through 5, and 11 were not utilized in this Example. The extruder was used without the die system (zone 11) to allow for ease of material to exit extruder. The protein and thymol were pre-blended (17.3 wt % thymol) and subsequently added to the extruder at zone 6 at a feed rate of 0.5 lbs/hr. Lactic acid was then added at zone 7 at a feed rate of 0.087 lb/hr to give a composition of 70.4% WhetPro®, 14.8% lactic acid, 14.7% thymol. The screw configuration was composed of conveying elements at zones 6 and 7, kneading blocks at zones 8 and 9, and conveying elements at zone 10. The screw speed was 50 rpm. The temperature profile for zones 6-10 was 24° C., 32° C., 42° C., 70° C., 70° C. respectively. The resulting material was contained in plastic bag and stored at −32° C. Cooled material was downsized via Brickmann/Retsch lab scale grinding mill (set speed=1) and collected at a size of 250 to 425 μm by sieving. The samples were tested for thymol stability after aging at 50° C. for 1, 4, 15, 18, 56, 104 days using the test methods described above. The results are set forth in Table 3.

TABLE 3

Thymol Level After Aging at 50° C.

| | Thymol Level (wt %) | | | | | |
|---|---|---|---|---|---|---|
| Example | 0 days | 1 days | 4 days | 15 days | 18 days | 56 days | 104 days |
| 3 | 14.3 | 14 | 12.4 | 9.1 | 8.2 | 7.55 | 7.09 |

EXAMPLE 4

A "PRISM USALAB 16" lab scale twin screw extruder was employed to melt process WhetPro® 75 Gluten and thymol. The extruder contained eleven (11) different zones, although zones 1 through 5, and 11 were not utilized in this Example. The extruder used a 0.75-inch die system (zone 11) to allow for ease of material to exit extruder. The protein and thymol were pre-blended (17 wt % thymol and 83% protein) and subsequently added to the extruder at zone 6 at a feed rate of 0.5 lbs/hr to give a composition of 83% WhetPro® and 17% thymol. The screw configuration was composed of conveying elements at zones 6 and 7, kneading blocks at zones 8 and 9, and conveying elements at zone 10. The screw speed was 50 rpm. The temperature profile for zones 6-11 was 37° C., 47° C., 60° C., 70° C., 70° C., and 70° C., respectively. The resulting material was contained in plastic bag and stored at −32° C. Cooled material was downsized via Brickmann/Retsch lab scale grinding mill (set speed=1) and collected at a size <250 μm. The samples were tested for thymol stability after aging at 55° C. for 0, 14, 19 days. The results are set forth in Table 4.

TABLE 4

Thymol Level After Aging at 55° C.

| | Thymol Level (wt %) | | |
|---|---|---|---|
| Example | 0 days | 7 days | 19 days |
| 4 | 14.3 | 14 | 12.4 |

Figure 5:
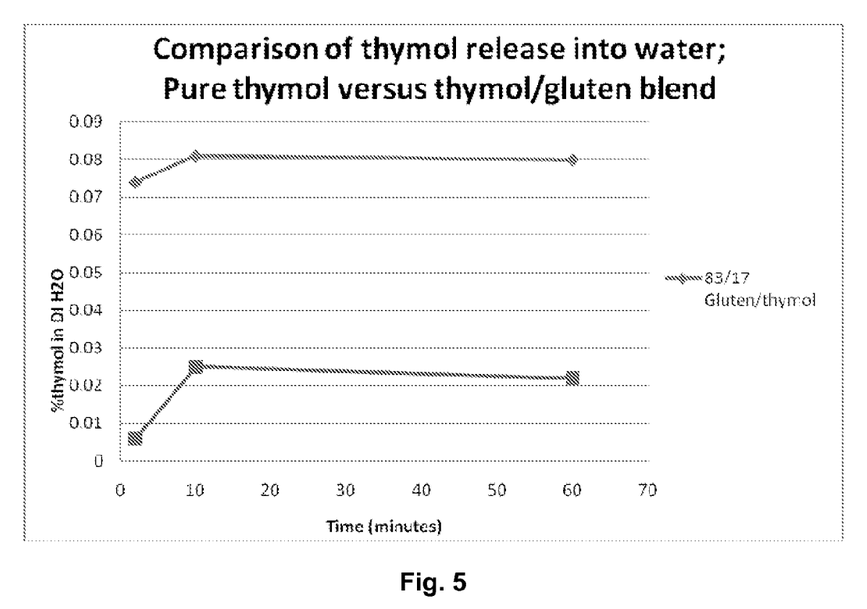
FIG. 5 is a graph of the results obtained in Example 3, in which the % thymol retained in water is shown for a period of time ranging from 0 to 60 minutes.

100 milliliters of deionized water was then added to 5.88 grams of the non-aged particles, as well as to 1 gram of neat thymol. The concentration of thymol in water was determined for samples extracted for 2, 10, and 60 minutes by the method entitled "Thymol Concentrations in Extractions." The results are shown in FIG. 5. As indicated, the amount of thymol released into water from the thymol/protein particle was approximately four (4) times greater than a sample extracted from neat thymol.

EXAMPLE 5

A "PRISM USALAB 16" lab scale twin screw extruder was employed to melt process two (2) different samples of WhetPro® 75 (gluten), glycerol, and volatile oil (carvacrol or eucalyptol). The extruder contained eleven (11) different zones, although zones 1 through 5 were not utilized in this Example. Temperature zone 11 was a strand die. WhetPro® 75 was added to the extruder at zone 6 via a drop feeder at a feed rate of 0.5 lbs/hr. Glycerol and the volatile oil were then added via a syringe pump at zone 7 at a feed rate of 0.24 lb/hr. The formulation was set to contain 81 wt. % WhetPro® 75, 11 wt. % glycerol, and 5 wt. % of volatile oil. The screw configuration was composed of conveying elements at zones 6 and 7, kneading blocks at zones 8 and 9, and conveying elements at zone 10. The screw speed was 100 rpm. The temperature profile for the samples are set forth below.

| Sample | Volatile Oil | Pellet Size (mm) | Target Temp. (° C.) | Temperature Profile (° C.) | | | | | |
|---|---|---|---|---|---|---|---|---|---|
| | | | | Zone 6 | Zone 7 | Zone 8 | Zone 9 | Zone 10 | Zone 11 |
| 7 | Carvacrol | 3 | 70 | ~35 | ~40 | ~55 | 70 | 70 | 70 |
| 8 | Eucalyptol | 3 | 70 | ~35 | ~40 | ~55 | 70 | 70 | 70 |

Once formed, the samples were put into an airtight bag and placed in −10° C. freezer. The resulting samples were tested for volatile oil stability using the test method described above. The results are set forth below in Table 5.

TABLE 5

Volatile Oil Level After Aging at 50° C.

| | Volatile Oil level (wt. %) | | | | |
|---|---|---|---|---|---|
| Sample | 0 days | 5 days | 10 days | 20 days | 40 days |
| 7 | 3.70 | 3.80 | 3.00 | 3.10 | 2.95 |
| 8 | 1.66 | 1.54 | 1.53 | 0.43 | 0.59 |

EXAMPLE 6

A "PRISM USALAB 16" lab scale twin screw extruder was employed to melt process WhetPro® 75, glycerol, and thymol. The extruder contained eleven (11) different zones, although zones 1 through 5, and 11 were not utilized in this Example. The extruder was used with a 0.75-inch die system (zone 11) to allow for ease of material to exit extruder. The protein and thymol were pre-blended (17.3 wt % thymol) and subsequently added to the extruder at zone 6 at a feed rate of 0.5 lbs/hr. Glycerol was then added at zone 7 at a feed rate of 0.087 lb/hr check process rounds to give a approximate composition of 71% WhetPro®, 14% glycerol, 15% thymol. The screw configuration was composed of conveying elements at zones 6 and 7, kneading blocks at zones 8 and 9, and conveying elements at zone 10. The screw speed was 50 rpm. The temperature profile for zones 9-11 was 70° C. The resulting material was contained in plastic bag and stored at −32° C. Cooled material was downsized via Brickmann/Retsch lab scale grinding mill (set speed=1) and collected at a size of: <250, 250-425, 425-710, 710-1000 μm by sieving. The resulting samples were tested for thymol stability at 55° C. using the test method described above. The results are set forth below in Table 6.

TABLE 6

Rate Loss of Thymol for Various Particle Size Ranges

| Particle Size (microns) | % Thymol (w/w) after 7 day aging | Rate loss (%/day) |
|---|---|---|
| <250* | 2.3 | 12.1 |
| 250-425 | 5.7 | 8.9 |
| 425-710 | 6.7 | 7.9 |
| 710-1000 | 8.0 | 6.7 |

*An example calculation for the "rate loss" is as follows: [(15% initial thymol – 2.3% thymol aged) ÷ 15% initial thymol] ÷ 7 days * 100 = 12.1%/day As indicated, the amount of thymol lost from the thymol/protein particle was dependent on particle size in that the loss was significantly increased for particles having a smaller particle size.

EXAMPLE 7

A composition of 71% WhetPro®, 14% glycerol, 15% thymol was prepared and downsized as described in Example 6. Particle size ranges of <250, 250-425, and >425 microns were collected via seiving. Once formed, 100 milliliters of deionized water was added to 6.67 grams of the non-aged particles. The concentration of thymol in water was determined after 10 minutes of extraction in water by the method described above. The results are shown in Table 7.

TABLE 7

Thymol Released for Various Particle Sizes

| Particle Size (microns) | % Thymol in water (% wt) |
|---|---|
| <250 | 0.062 |
| 250-425 | 0.0296 |
| >425 | 0.017 |

As indicated, the amount of thymol released into water from the thymol/protein particle was dependent on particle size in that the concentration of thymol was increase for reduced particle sizes.

EXAMPLE 8

A composition of 71% WhetPro®, 14% glycerol, 15% thymol was prepared and downsized as described in Example 6. The particle size range of <250 was collected via seiving. Once formed, 50 milliliters of deionized water was added to 6.67 grams of the non-aged particles. The concentration of thymol in water was determined at 2, 10, and 60 minutes by the method described above giving thymol concentrations by weight of 0.058%, 0.057%, 0.072% respectively.

EXAMPLE 9

A composition of 71% WhetPro®, 14% glycerol, 15% thymol was prepared and downsized as described in Example 6. The particle size range of <250 was collected via seiving. Once formed, 100 milliliters of ethanol was added to 6.67 grams of the non-aged particles. The concentration of thymol in ethanol was determined at 2, 10, and 60 minutes by the method described above giving thymol concentrations by weight of 0.255, 0.260%, 0.292% respectively.

EXAMPLE 10

A composition of 71% WhetPro®, 14% glycerol, 15% thymol was prepared by extrusion and downsized as described in Example 6. The particle size range of 250-425 collected via seiving. Once formed, 100 milliliters of $7.7 \times 10^{-6}$ M citric acid in deionized water was added to 6.67 grams of the non-aged particles. The concentration of thymol in solution was determined after extraction for 10 minutes by the method described above giving a thymol concentration by weight of 0.032%.

EXAMPLE 11

A composition of 71% WhetPro®, 14% glycerol, 15% thymol was prepared by extrusion and downsized as described in Example 6. The particle size range of 250-425 was collected via seiving. Once formed, 100 milliliters of 7.5% citric acid by weight in deionized water was added to 6.67 grams of the non-aged particles. The concentration of thymol in solution was determined after extraction for 10 minutes by the method described above giving thymol concentration by weight of 0.046%.

EXAMPLE 12

A composition of 81% WhetPro®, 14% glycerol, 5% thymol was prepared by extrusion and downsized as described in Example 6. The particle size range of <250 micron was collected via seiving. Once formed, 100 milliliters of 0.1% aqueous acetic acid was added to 20 grams of the non-aged particles. The concentration of thymol in acetic acid solution was determined after extraction for 2, 10, and 60 minutes by the method described above giving thymol concentrations by weight of 0.069%, 0.080%, 0.083% respectively.

EXAMPLE 13

Various compositions containing different thymol concentrations were extruded and downsized to particle size of <250 microns. The resulting samples were tested for thymol stability at 55° C. using the test method described above. The results are set forth in Table 8.

TABLE 8

Thymol Level After Aging at 55° C.

| Composition | | | Thymol Level (wt %) | | |
|---|---|---|---|---|---|
| Protein | Carrier Fluid | % Thymol Add-On | 0 days | 7 days | 19 days |
| 71% Gluten | 14% glycerol | 15 | 14.3 | 2.3 | 1.3 |
| 81% Gluten | 14% glycerol | 5 | 4.6 | 3 | 2.6 |
| 85% Gluten | 14% glycerol | 1 | 1 | 0.7 | 0.7 |

Table 8 illustrates that thymol loss was dependent on thymol concentration and time. For example, higher concentrations resulted in a higher thymol loss. Likewise, a longer aging time resulted in a lower rate loss of thymol. Table 9 summarizes the thymol rate loss for each composition at each aging time interval of 0 days to 7 and 7 days to 19 days.

TABLE 9

Thymol Rate Loss

| Particle Composition | | | Thymol Rate loss (%/day) | |
| --- | --- | --- | --- | --- |
| Protein | Carrier Fluid | % Thymol | From 0 to 7 days | From 7 to 19 days |
| 71% Gluten | 14% glycerol | 15 | 1.71 | 0.08 |
| 81% Gluten | 14% glycerol | 5 | 0.23 | 0.03 |
| 85% Gluten | 14% glycerol | 1 | 0.04 | 0.00 |

EXAMPLE 14

A composition of 71% WhetPro®, 14% glycerol, 15% thymol was prepared by extrusion and downsized as described in Example 6. The particle size range of 250-425 micron was collected via sieving.

A series of thymol extractions were carried out from the particles prepared in Example 14 that involved various amounts of thymol/protein particles, various amounts of water, addition of citric acid particles, and extracting time. The extracting method involved adding specified amount of water to protein/thymol particles and citric acid particles, waiting a specified amount of time while shaking, and centrifuging to collect supernatant. In addition, water was added to neat thymol as a control, shaken for specified amount of time, and centrifuged to collect supernatant. The thymol concentration in supernatant was determined by the method described above. The composition of the solutions and the resulting thymol concentration are set forth in Table 10.

TABLE 10

Thymol Extractions from Particles
Particle Composition

| Protein | Carrier Fluid | % Thymol | Particle Size (microns) | Amount (grams) | Citric acid (grams) | Deionized water (milliliters) | Extracting time (mins) | % Thymol (wt/wt) in extract solution |
| --- | --- | --- | --- | --- | --- | --- | --- | --- |
| 71% Gluten | 14% glycerol | 15% | 250-425 | 0.75 | 0.38 | 12.4 | 30 | 0.557 |
| | | | | 1.5 | 0.38 | 12.4 | 30 | 1.115 |
| | | | | 0.75 | 0.38 | 12.4 | 10 | 0.509 |
| | | | | 0.75 | 0 | 12.4 | 30 | 0.048 |
| | | | | 2.25 | 1.14 | 37.2 | 30 | 0.610 |
| n/a | n/a | 100 (control) | <250 | 2 | 1.14 | 97 | 30 | 0.081 |
| | | | | 2 | 0 | 100 | 30 | 0.084 |

The reported solubility limit of thymol in water is normally is 0.1 grams per 100 grams of water (0.1%) at 25° C. As illustrated above, however, the concentrations of thymol in the extract solutions were up to 11 times greater than the reported limited solubility. Two of the solutions above (0.557% thymol and 1.115% thymol) were also tested for antimicrobial efficacy according to the microplate assay described above. The results are set forth below in Table 11.

TABLE 11

Efficacy of Thymol Extractions

| Example | Protein | Carrier Fluid | % Thymol | Particle Size (microns) | Amount (grams) | # of wells showing growth after test for S. aureus | # of wells showing growth after test for P. aeruginosa |
| --- | --- | --- | --- | --- | --- | --- | --- |
| 15 | 71% Gluten | 14% glycerol | 15 | 250-425 | 0.75 | 1 | 1 |
| 16 | | | | | 1.5 | 3 | 1 |

While the invention has been described in detail with respect to the specific embodiments thereof, it will be appreciated that those skilled in the art, upon attaining an understanding of the foregoing, may readily conceive of variations and equivalents to these embodiments. Accordingly, the scope of the present invention should be assessed as that of the appended claims and any equivalents thereto.

What is claimed is:

1. A melt-processed antimicrobial composition comprising at least one monoterpene phenol in an amount of from about 0.1 wt. % to about 30 wt. %, at least one melt-processible plant protein in an amount of from about 30 wt. % to about 95 wt. %, and at least one carrier fluid in amount of from about 1 wt. % to about 50 wt. %.

2. The composition of claim 1, wherein the monoterpene phenol is thymol, carvacrol, or a mixture thereof.

3. The composition of claim 1, wherein the plant protein is wheat gluten.

4. The composition of claim 1, wherein the carrier fluid is a polyhydric alcohol.

5. The composition of claim 4, wherein the polyhydric alcohol is glycerol.

6. The composition of claim 1, wherein the carrier fluid is an aliphatic carboxylic acid.

7. The composition of claim 1, wherein monoterpene phenols constitute from about 0.5 wt. % to about 20 wt. % of the composition, melt-processible plant proteins constitute from about 40 wt. % to about 90 wt. % of the composition, and carrier fluids constitute from about 5 wt. % to about 30 wt. % of the composition.

8. The composition of claim 1, wherein the composition is general free of solvents.

9. The composition of claim 1, wherein the composition is in the form of particles.

10. The composition of claim 9, wherein the particles have an average size of from about 100 to about 600 micrometers.

11. A wipe comprising the melt-processed antimicrobial composition of claim 1, wherein the wipe includes a fibrous material.

12. The wipe of claim 11, wherein the fibrous material contains absorbent fibers.

13. The wipe of claim 12, wherein the fibrous material is a composite of absorbent fibers and synthetic thermoplastic fibers.

14. A method for removing bacteria from a surface, the method comprising contacting the surface with a wipe that comprises a fibrous material that contains a melt-processed antimicrobial composition comprising at least one monoterpene phenol in an amount of from about 0.1 wt. % to about 30 wt. %, at least one melt-processible plant protein in an amount of from about 30 wt. % to about 95 wt. %, and at least one carrier fluid in amount of from about 1 wt. % to about 50 wt. %.

15. The method of claim 14, wherein prior to contacting the surface with the wipe, an aqueous solution is applied to the composition to release the monoterpene phenol.

16. The method of claim 15, wherein the concentration of the monoterpene phenol released in the aqueous solution is greater than about 0.1 wt. %.

17. The method of claim 15, wherein the concentration of the monoterpene phenol released in the aqueous solution is from about 1 wt. % to about 10 wt. %.

18. The method of claim 15, wherein the aqueous solution contains an acid.

19. The method of claim 14, wherein the composition is in the form of particles.

20. The method of claim 19, wherein the particles have an average size of from about 100 to about 600 micrometers.

\* \* \* \* \*